(12) United States Patent
Feld et al.

(10) Patent No.: US 10,220,193 B2
(45) Date of Patent: Mar. 5, 2019

(54) DEVICE FOR COMPARTMENTAL DILATATION OF BLOOD VESSELS (71) Applicant: Quattro Vascular PTE Ltd., SGX Centre 1 (SG)

(72) Inventors: Tanhum Feld, Moshav Merhavya (IL); Eitan Konstantino, Orinda, CA (US)

(73) Assignee: TriReme Medical, LLC, Pleasanton, CA (US)

( * ) Notice: Subject to any disclaimer, the term of this patent is extended or adjusted under 35 U.S.C. 154(b) by 322 days.

(21) Appl. No.: 14/807,657

(22) Filed: Jul. 23, 2015

(65) Prior Publication Data

US 2016/0022968 A1 Jan. 28, 2016

Related U.S. Application Data

(63) Continuation of application No. 13/756,250, filed on Jan. 31, 2013, now abandoned.

(60) Provisional application No. 61/593,704, filed on Feb. 1, 2012.

(51) Int. Cl.
*A61M 25/10* (2013.01)
*A61M 29/02* (2006.01)

(52) U.S. Cl.
CPC .. *A61M 25/10184* (2013.11); *A61M 25/1002* (2013.01); *A61M 25/104* (2013.01); *A61M 29/02* (2013.01); *A61M 2025/105* (2013.01); *A61M 2025/1081* (2013.01); *A61M 2025/1084* (2013.01)

(58) Field of Classification Search
CPC ......... A61M 2025/1084; A61M 1/0015; A61F 2/04; A61F 2/07; A61F 2/82; A61F 2002/828; A61F 2/86
See application file for complete search history.

(56) References Cited

U.S. PATENT DOCUMENTS

| 2,701,559 | A | 2/1955 | Cooper |
| 2,854,983 | A | 10/1958 | Baskin |
| 3,045,677 | A | 7/1962 | Wallace |
| 3,467,101 | A | 9/1969 | Fogarty et al. |
| 3,825,013 | A | 7/1974 | Craven |

(Continued)

FOREIGN PATENT DOCUMENTS

| CN | 1568165 A | 1/2005 |
| EP | 0 565 796 | 10/1993 |

(Continued)

OTHER PUBLICATIONS

AngioSculpt XL PT Scoring Balloon Catheter Brochure, AngioScore, Inc., Rev. C, May 2013.

(Continued)

*Primary Examiner* — Quynh-Nhu H. Vu
(74) *Attorney, Agent, or Firm* — Knobbe Martens Olson & Bear LLP (57) ABSTRACT

A constraining structure for use with a balloon catheter includes multiple longitudinal struts and multiple expandable radial rings. The constraining structure can expand radially but may not expand substantially in the longitudinal direction. The constraining structure can have multiple compartments configured to expand independently of one another. Inflating the balloon catheter within the constraining structure can allow for dilation of the blood vessel in a pre determined topography.

14 Claims, 7 Drawing Sheets

(56) References Cited

U.S. PATENT DOCUMENTS

| | | | |
|---|---|---|---|
| 4,327,736 A | 5/1982 | Inoue | |
| 4,456,011 A | 6/1984 | Warnecke | |
| 4,483,340 A | 11/1984 | Fogarty et al. | |
| 4,637,396 A | 1/1987 | Cook | |
| 4,723,549 A | 2/1988 | Wholey et al. | |
| 4,796,629 A | 1/1989 | Grayzel | |
| 4,921,484 A | 5/1990 | Hillstead | |
| 4,976,711 A | 12/1990 | Parins et al. | |
| 4,998,539 A | 3/1991 | Delsanti | |
| 5,071,407 A | 12/1991 | Porter et al. | |
| 5,100,386 A | 3/1992 | Inoue | |
| 5,133,732 A | 7/1992 | Wilkor | |
| 5,176,693 A | 1/1993 | Pannek | |
| 5,181,911 A | 1/1993 | Shturman | |
| 5,190,058 A | 3/1993 | Jones et al. | |
| 5,196,024 A | 3/1993 | Barath | |
| 5,222,971 A | 6/1993 | Willard et al. | |
| 5,224,945 A | 7/1993 | Pannek, Jr. | |
| 5,263,963 A | 11/1993 | Garrison et al. | |
| 5,308,356 A | 5/1994 | Blackshear, Jr. et al. | |
| 5,320,634 A | 6/1994 | Vigil et al. | |
| 5,336,178 A | 8/1994 | Kaplan | |
| 5,336,234 A | 8/1994 | Vigil et al. | |
| 5,344,419 A | 9/1994 | Spears | |
| 5,449,372 A | 9/1995 | Schmaltz et al. | |
| 5,456,666 A | 10/1995 | Campbell et al. | |
| 5,456,667 A | 10/1995 | Ham et al. | |
| 5,460,607 A | 10/1995 | Miyata et al. | |
| 5,484,411 A | 1/1996 | Inderbitzen et al. | |
| 5,501,694 A | 3/1996 | Ressemann et al. | |
| 5,527,282 A | 6/1996 | Segal | |
| 5,556,408 A | 9/1996 | Farhat | |
| 5,562,620 A | 10/1996 | Klein et al. | |
| 5,571,086 A | 11/1996 | Kaplan et al. | |
| 5,607,442 A | 3/1997 | Fischell et al. | |
| 5,609,574 A | 3/1997 | Kaplan et al. | |
| 5,616,149 A | 4/1997 | Barath | |
| 5,620,457 A | 4/1997 | Pinchasik et al. | |
| 5,628,746 A | 5/1997 | Clayman | |
| 5,628,755 A | 5/1997 | Heller et al. | |
| 5,643,210 A | 7/1997 | Iacob | |
| 5,643,312 A * | 7/1997 | Fischell | A61F 2/844 606/198 |
| 5,695,469 A | 12/1997 | Segal | |
| 5,702,410 A | 12/1997 | Klunder et al. | |
| 5,713,863 A | 2/1998 | Vigil et al. | |
| 5,730,698 A | 3/1998 | Fischell et al. | |
| 5,733,303 A | 3/1998 | Israel et al. | |
| 5,735,816 A | 4/1998 | Lieber et al. | |
| 5,755,781 A | 5/1998 | Jayaraman | |
| 5,772,681 A | 6/1998 | Leoni | |
| 5,776,181 A | 7/1998 | Lee et al. | |
| 5,797,935 A | 8/1998 | Barath | |
| 5,810,767 A | 9/1998 | Klein | |
| 5,827,321 A | 10/1998 | Roubin et al. | |
| 5,863,284 A | 1/1999 | Klein | |
| 5,868,708 A | 2/1999 | Hart et al. | |
| 5,868,719 A | 2/1999 | Tsukernik | |
| 5,868,779 A | 2/1999 | Ruiz | |
| 5,868,783 A | 2/1999 | Tower | |
| 5,869,284 A | 2/1999 | Cao et al. | |
| 5,904,679 A | 5/1999 | Clayman | |
| 5,906,639 A | 5/1999 | Rudnick et al. | |
| 5,919,200 A | 7/1999 | Stambaugh et al. | |
| 5,961,490 A | 10/1999 | Adams | |
| 5,967,984 A | 10/1999 | Chu et al. | |
| 5,987,661 A | 11/1999 | Peterson | |
| 6,013,055 A | 1/2000 | Bampos et al. | |
| 6,036,689 A | 3/2000 | Tu et al. | |
| 6,036,708 A | 3/2000 | Sciver | |
| 6,053,913 A | 4/2000 | Tu et al. | |
| 6,059,811 A | 5/2000 | Pinchasik et al. | |
| 6,077,298 A | 6/2000 | Tu et al. | |
| 6,102,904 A | 8/2000 | Vigil et al. | |
| 6,106,548 A | 8/2000 | Roubin et al. | |
| 6,129,706 A | 10/2000 | Janacek | |
| 6,156,265 A | 12/2000 | Sugimoto | |
| 6,190,403 B1 | 2/2001 | Fischell et al. | |
| 6,206,910 B1 | 3/2001 | Berry et al. | |
| 6,217,608 B1 | 4/2001 | Penn et al. | |
| 6,235,043 B1 | 5/2001 | Reiley et al. | |
| 6,241,762 B1 | 6/2001 | Shanley | |
| 6,245,040 B1 * | 6/2001 | Inderbitzen | A61M 25/104 604/103.07 |
| 6,261,319 B1 | 7/2001 | Kveen et al. | |
| 6,309,414 B1 | 10/2001 | Rolando et al. | |
| 6,319,251 B1 | 11/2001 | Tu et al. | |
| 6,361,545 B1 | 3/2002 | Macoviak et al. | |
| 6,416,539 B1 | 7/2002 | Hassdenteufel | |
| 6,454,775 B1 | 9/2002 | Demarais et al. | |
| 6,540,722 B1 | 4/2003 | Boyle et al. | |
| 6,605,107 B1 | 8/2003 | Klein | |
| 6,616,678 B2 | 9/2003 | Nishtala et al. | |
| 6,626,861 B1 | 9/2003 | Hart et al. | |
| 6,652,548 B2 | 11/2003 | Evans et al. | |
| 6,656,351 B2 | 12/2003 | Boyle | |
| 6,695,813 B1 | 2/2004 | Boyle et al. | |
| 6,702,834 B1 | 3/2004 | Boylan et al. | |
| 6,939,320 B2 | 9/2005 | Lennox | |
| 6,942,680 B2 | 9/2005 | Grayzel et al. | |
| 7,186,237 B2 | 3/2007 | Meyer et al. | |
| 7,357,813 B2 | 4/2008 | Burgermeister | |
| 7,686,824 B2 | 3/2010 | Konstantino et al. | |
| 7,691,119 B2 | 4/2010 | Farnan | |
| 7,708,748 B2 | 5/2010 | Weisenburgh, II et al. | |
| 7,753,907 B2 * | 7/2010 | DiMatteo | A61B 18/1492 606/159 |
| 7,803,149 B2 | 9/2010 | Bates et al. | |
| 7,931,663 B2 | 4/2011 | Farnan et al. | |
| 8,172,793 B2 | 5/2012 | Bates et al. | |
| 8,257,305 B2 | 9/2012 | Speck et al. | |
| 8,388,573 B1 | 3/2013 | Cox | |
| 8,439,868 B2 | 5/2013 | Speck et al. | |
| 9,179,936 B2 | 11/2015 | Feld et al. | |
| 9,199,066 B2 | 12/2015 | Konstantino et al. | |
| 9,216,033 B2 | 12/2015 | Feld et al. | |
| 9,375,328 B2 | 6/2016 | Farnan | |
| 9,415,140 B2 | 8/2016 | Speck | |
| 9,649,476 B2 | 5/2017 | Speck et al. | |
| 2002/0010489 A1 | 1/2002 | Grayzel et al. | |
| 2003/0023200 A1 | 1/2003 | Barbut et al. | |
| 2003/0040790 A1 | 2/2003 | Furst | |
| 2003/0078606 A1 | 4/2003 | Lafontaine et al. | |
| 2003/0114915 A1 | 6/2003 | Mareiro et al. | |
| 2003/0153870 A1 | 8/2003 | Meyer et al. | |
| 2003/0195609 A1 | 10/2003 | Berenstein et al. | |
| 2004/0034384 A1 | 2/2004 | Fukaya | |
| 2004/0073284 A1 | 4/2004 | Bates et al. | |
| 2004/0143287 A1 | 7/2004 | Konstantino et al. | |
| 2004/0210235 A1 | 10/2004 | Deshmukh | |
| 2004/0210299 A1 | 10/2004 | Rogers et al. | |
| 2004/0230293 A1 | 11/2004 | Yip et al. | |
| 2005/0021071 A1 | 1/2005 | Konstantino et al. | |
| 2005/0125053 A1 * | 6/2005 | Yachia | A61F 2/844 623/1.15 |
| 2005/0271844 A1 | 12/2005 | Mapes et al. | |
| 2006/0008606 A1 | 1/2006 | Horn et al. | |
| 2006/0015133 A1 | 1/2006 | Grayzel et al. | |
| 2006/0085025 A1 * | 4/2006 | Farnan | A61B 17/320725 606/194 |
| 2006/0259005 A1 * | 11/2006 | Konstantino | A61B 17/22032 604/500 |
| 2006/0271093 A1 | 11/2006 | Holman et al. | |
| 2007/0073376 A1 | 3/2007 | Krolik et al. | |
| 2007/0173923 A1 * | 7/2007 | Savage | A61F 2/91 623/1.15 |
| 2008/0255508 A1 * | 10/2008 | Wang | A61K 31/337 604/103.02 |
| 2009/0038752 A1 | 2/2009 | Weng et al. | |
| 2009/0105686 A1 | 4/2009 | Snow et al. | |
| 2009/0192453 A1 | 7/2009 | Wesselman | |
| 2009/0227949 A1 | 9/2009 | Knapp et al. | |
| 2009/0240270 A1 | 9/2009 | Schneider et al. | |
| 2009/0319023 A1 | 12/2009 | Hildebrand et al. | |

(56) References Cited

U.S. PATENT DOCUMENTS

| | | |
|---|---|---|
| 2010/0042121 A1 | 2/2010 | Schnieder et al. |
| 2010/0234875 A1 | 9/2010 | Allex et al. |
| 2010/0331809 A1 | 12/2010 | Sandhu et al. |
| 2011/0071616 A1 | 3/2011 | Clarke et al. |
| 2011/0172698 A1 | 7/2011 | Davies et al. |
| 2012/0059401 A1* | 3/2012 | Konstantino ........... A61F 2/958 606/159 |
| 2012/0083733 A1 | 4/2012 | Chappa |
| 2012/0245607 A1 | 9/2012 | Gershony et al. |
| 2013/0046237 A1 | 2/2013 | Speck et al. |
| 2013/0116655 A1 | 5/2013 | Bacino et al. |
| 2013/0190725 A1 | 7/2013 | Pacetti et al. |
| 2013/0211381 A1 | 8/2013 | Feld |
| 2013/0218181 A1 | 8/2013 | Feld et al. |
| 2014/0066960 A1 | 3/2014 | Feld et al. |
| 2015/0209556 A1 | 7/2015 | Timothy |
| 2016/0058991 A1 | 3/2016 | Feld et al. |
| 2016/0100964 A1 | 4/2016 | Feld et al. |
| 2016/0136397 A1 | 5/2016 | Konstantino et al. |

FOREIGN PATENT DOCUMENTS

| | | |
|---|---|---|
| EP | 0 623 315 | 11/1994 |
| EP | 0 832 608 | 4/1998 |
| EP | 1 042 997 | 10/2000 |
| JP | 2005-508709 | 4/2005 |
| WO | WO 98/05377 | 2/1998 |
| WO | WO 98/50101 | 11/1998 |
| WO | WO 2002/068011 | 9/2002 |
| WO | WO 2003/041760 | 5/2003 |
| WO | WO 2005/020855 | 3/2005 |
| WO | WO 2011/112863 | 9/2011 |
| WO | WO 2013/114201 | 8/2013 |
| WO | WO 2013/119735 | 8/2013 |

OTHER PUBLICATIONS

Kadish, A., et al. "Mapping of Atrial Activation With a Noncontact, Multielectrode Catheter in Dogs," *Circulation: Journal of the American Heart Association*, (Apr. 1999) 99: 1906-1913.

International Search Report for Appl. No. PCT/US2011/027982 dated May 6, 2011 in 3 pages.

International Search Report for Appl. No. PCT/IB13/00217, dated Jun. 14, 2013 in 7 pages.

International Search Report for Appl. No. PCT/US13/25032, dated Apr. 19, 2013 in 8 pages.

Brydson, J.A., "Plastics Materials—Sixth Edition," 1995, p. 510, available in part online from https://books.google.com/books?id=wmohBQAAQBAJ&lpg=PA510&ots=G4Q-OMpB4&dq=young's%20modulus%20of%20PEBAx&pg=PA510#v=onepage&q=young's%20modulus%20of%20PEBAx&f=false; printed on May 5, 2017.

"Materials Data Book," Cambridge University Engineering Department, 2003, pp. 1-41.

Bearing Works, (PTFE) Polytetrafluoroethylene material specifications sheet, available online Feb. 11, 2018 at https://www.bearingworks.com/uploaded-assets/pdfs/retainers/ptfe-datasheet.pdf; printed Feb. 21, 2018, in 2 pages.

* cited by examiner

FIG. 1A  Pre-inflation
FIG. 1B  During inflation
FIG. 1C  End of inflation

DEVICE FOR COMPARTMENTAL DILATATION OF BLOOD VESSELS

This application is a continuation of U.S. patent application Ser. No. 13/756,250, filed Jan. 31, 2013, which claims the benefit of U.S. Provisional Application No. 61/593,704, filed Feb. 1, 2012, the entirety of which is incorporated by reference herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Field of the Invention

The present invention relates to the field of medical methods and devices, specifically to medical dilatation balloon catheters and devices intended to treat blood vessel obstructions and/or deliver active substance to body tissue.

Angioplasty balloons are one of the most commonly used tools for treatment of narrowed and occluded blood vessels. These balloons are typically cylindrical when inflated and are manufactured in various dimensions (length and diameter) to conform to different vessel size. Balloons are located at the distal end of flexible catheters and delivered to a target site/lesion where they are inflated, normally between 8-20 atmospheres, in order to overcome the resistance of the lesion and achieve luminal expansion. Such high pressure angioplasty is often associated with trauma to the vessel walls with a resulting high frequency of vessel dissection (30%-40%), abrupt closure of the treated vessel (5%-12%), and restenosis. When conventional angioplasty is used as a primary treatment for occluded vessels, restenosis can occur in about 50% of the cases. Therefore in the vast majority of coronary treatments, angioplasty is used as an initial treatment followed by placement of a stent. Frequently the stents are coated with drug and polymer requiring the patient to take anti platelet therapy for extended periods, possibly lifelong, to limit the risk of stent thrombosis or blood clots.

In a standard balloon in order for the inflation to be effective it is necessary to apply more and more pressure until the stenosis gives way. This is an abrupt and forceful process that may result in severe trauma to the vessel wall that in the best case further delays the healing of the lesion and in the worst and not uncommon case result in dissections, abrupt closure and restenosis.

Figure 1A:
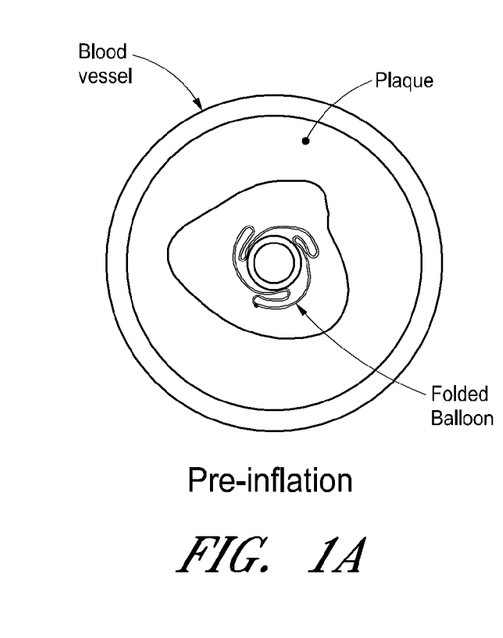
FIG. 1A to 1C show a cross-section of the stages of unwrapping of conventional balloon inflation in a stenotic blood vessel.
Figure 1B:
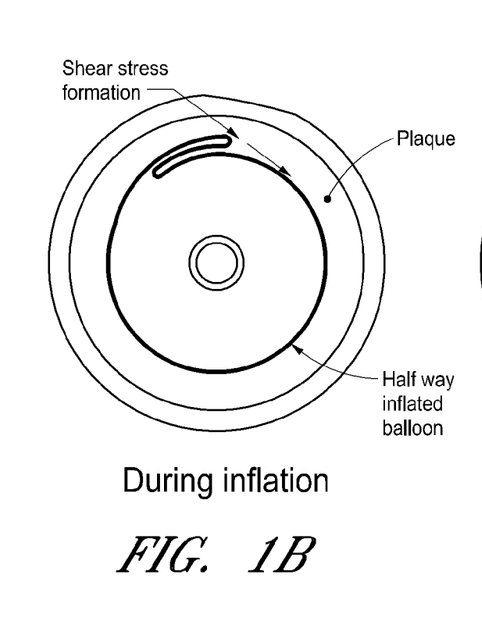
Figure 1C:
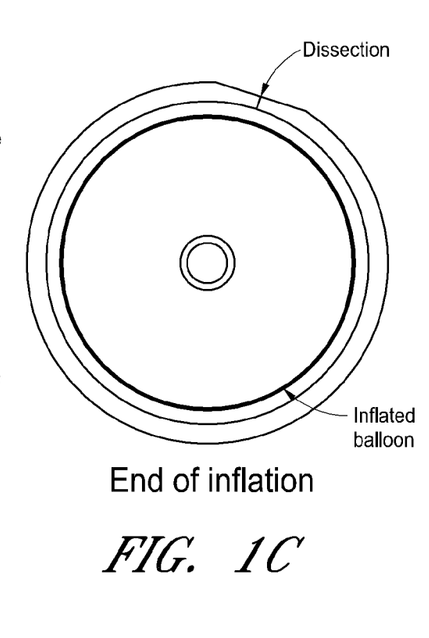

Dissections in the treated blood vessel due to balloon dilation are very common. The dissection rate is estimated as high as 30% of the cases. Some of these are severe and may require urgent surgery or placement of additional stents. In addition, dissection may contribute to poor long term clinical results and restenosis even if a stent is placed in the treated lesion. Dissections are attributed to several mechanisms occurring during balloon inflation including the shear forces applied on the vessel walls as the balloon pleats unfold and uneven inflation of the balloon due to inconsistency of the disease in the vessel. During inflation, while the balloon diameter increases in the radial direction, the folded balloon is unwrapped and applies tangential forces (See FIGS. 1A, 1B and 1C). Attempts have been made to resolve this problem by providing fully elastic or stretchable balloons that open radially without unfolding. However, those balloons, made of elastic materials could not provide sufficient dilatation forces since the materials are soft and compliant not capable of high pressure inflation.

The disease is not uniform and the inner diameter of the vessel can be characterized as anisotropic. Standards angioplasty balloons are commonly elastic or semi-compliant, and are designed to increase their diameter, and therefore apply force on the surrounding area in a uniform way. When inflated against an inconsistent resistance (eccentric lesions, focal plaque) it will be necessary to apply increased pressure until the plaque gives way and the balloon is fully inflated. This abrupt and uncontrolled process causes increased trauma to the area. Furthermore, at the initial stage of the elastic nature of a balloon cause its diameter to increase more at the elastic (and less diseased) areas of the vessel causing further trauma and delayed healing.

Long lesions (typical of peripheral lesions) create additional challenges. These lesions often require repeated inflation/deflations while progressing through the occluded vessel. This requires a consistency in the quality of performance that is not typical to balloons. Furthermore angioplasty balloons lengthen during dilation (up to 10%), this may cause further damage to non-diseased areas. Since the lengthening of the balloon is relative to its length, this is especially pronounced in treating long lesions.

Dissections, elastic recoil and abrupt closure are all mechanisms associated with current angioplasty balloons having a high level of injury and trauma to the treated vessel.

Therefore, it would be desirable to provide improved balloons and inflation structures for angioplasty balloons used in vascular treatments. In particular, a balloon that has less tendency to cause trauma and dissection to the blood vessel wall by modulating the inflation characteristics of the balloon and providing segmental compartmental dilation with local areas of compliance. Furthermore a controlled inflation that allows for a slow plaque remodeling and modification process can prove to be less traumatic and promote faster healing of the lesion.

It would be further desirable if the reduced dissections could also reduce the risk of elastic recoil and abrupt re-closure which are associated with current angioplasty balloons and their use. It would be further desired if such improved angioplasty balloon structures were compatible with each of stents, drug-eluting stents, and drug coated balloons. These advantages would preferably be obtained without loss of the ability of the catheters to increase the luminal size and restore blood vessel in the patient being treated. At least some of these objectives will be met by the invention as described hereinafter.

SUMMARY OF THE INVENTION

This invention discloses a device for angioplasty or dilatation of stenotic vessels and optionally for the delivery of active substance to the vessel wall. The balloon catheter disclosed here is designed to support a controlled and regulated plaque remodeling process promoting faster healing of the diseased area. This is achieved by modulation of the inflation characteristic resulting in less trauma to vessel wall during inflation.

This balloon catheter consists of a balloon catheter and a Constraining Structure (CS) located on the balloon portion of the catheter. The Constraining Structure (CS) serves to control and limit balloon inflation by modifying balloon topography and creating compartmental inflation where each inflation zone is independent of neighboring zones.

This topography helps to promote plaque remodeling during inflation and allow for a controlled inflation with minimized trauma to vessel wall. The CS also inhibits transfer of shear forces to the lesion and vessel wall as the balloon inflates.

As the balloon inflates both balloon and CS structure increase in diameter however the CS maximal diameter is smaller than the balloon diameter. The balloon continues to inflate through the CS creating a topography of hills (pillows) and valleys (CS locations). The CS and balloon are capable of expanding due to inflation force applied by balloon dilation. The CS expansion is limited by its geometrical design. The CS is designed to limit balloon diameter, to eliminate transfer of tangential forces to vessel wall and to allow a plaque remodeling process that minimizes trauma and promotes faster healing.

A conventional balloon is compliant or semi-compliant and has a smooth even surface. During inflation the balloon will expand more easily in areas of less resistance, such as the less diseased areas (see Image 4A to 4C). In order to successfully open the lesion it is necessary to apply more pressure then when pressure is high enough the lesion will "give in" and open abruptly. This inflation process is fast and aggressive and may cause severe trauma. The device described in this invention is designed to allow a slow process of plaque remodeling where the plaque is able to flow and reshape itself due to the topography created by the CS. It creates a series of cushions where the CS is located at valleys between them (see FIG. 3). The CS channels between the cushions prevent high pressure buildup in the plaque and over expansion of the dilated vessel thus minimizing trauma caused to vessel walls during inflation. Thus the inflation process is controlled resulting in less trauma to the vessel and faster healing of the area.

The CS is situated over the deflated and folded balloon and attached to the catheter near the distal end of the balloon or near the proximal end of the balloon or preferably both. It also can be placed over the balloon without attachment. Upon balloon inflation the CS expands and allows the dilatation of the vessel by the balloon in a pre determined topography. During balloon dilation both the balloon and the CS structure increase in diameter while length of the device does not change. This further modulates the mechanics of inflation by minimizing the creation of axial tension forces on the vessel wall. Unlike conventional balloons where the length of the balloon will increase up to 10% during inflation the CS structure and balloon effective length do not change. When balloon length is maintained throughout the inflation process it allows predictability and more control of the inflation mechanism, and the healthy areas of the vessel are not exposed to inflation and tension forces exposing them to further damage.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE PREFERRED EMBODIMENT

This invention discusses a device for treating of diseased, blocked, occluded or stenotic lumens in the body, typically blood vessels including both arteries and veins, and more typically coronary and peripheral arteries. This device dilates occluded vessels while causing minimal trauma to the lesion thus minimizing the risk of dissections, total occlusion, abrupt closure and restenosis, and promotes faster healing.

A Constraining Structure (CS) is placed over a balloon catheter where upon inflation both the balloon and the CS increase in diameter and during deflation the CS returns to its original dimensions. The CS can have multiple designs intended to expand to a diameter smaller than the maximal inflated diameter of the balloon. The CS can be connected to the balloon either on the distal side or the proximal side or both. It can also float over the balloon without firm attachment using simple covers since the CS can be designed to maintain its length during expansion and therefore there is no relative axial movement between the CS and the balloon. It can be made from various materials, processes and designs. It can be made from metal, preferable a very elastic metal such as Nitinol and it can be made from variety of polymers (e.g. Nylon). It can be constructed from wires or laser cut from a tube, sheath or other forms of materials.

In a preferred embodiment of this invention the CS is over the balloon. During inflation the CS expands allowing the balloon to expand under it. The maximum CS diameter is smaller than that of the inflated balloon, thus the balloon protrudes and expands through the CS creating a topography of hills and valleys. The CS structure creates a combination of a designed topography and controlled, slower inflation promoting a process of plaque remodeling. The plaque in the diseased area of the vessel is able to flow through the valleys in the designed topography, and re-distribute in the vessel allowing a gradual inflation without the need to apply added pressure.

Figure 2A:
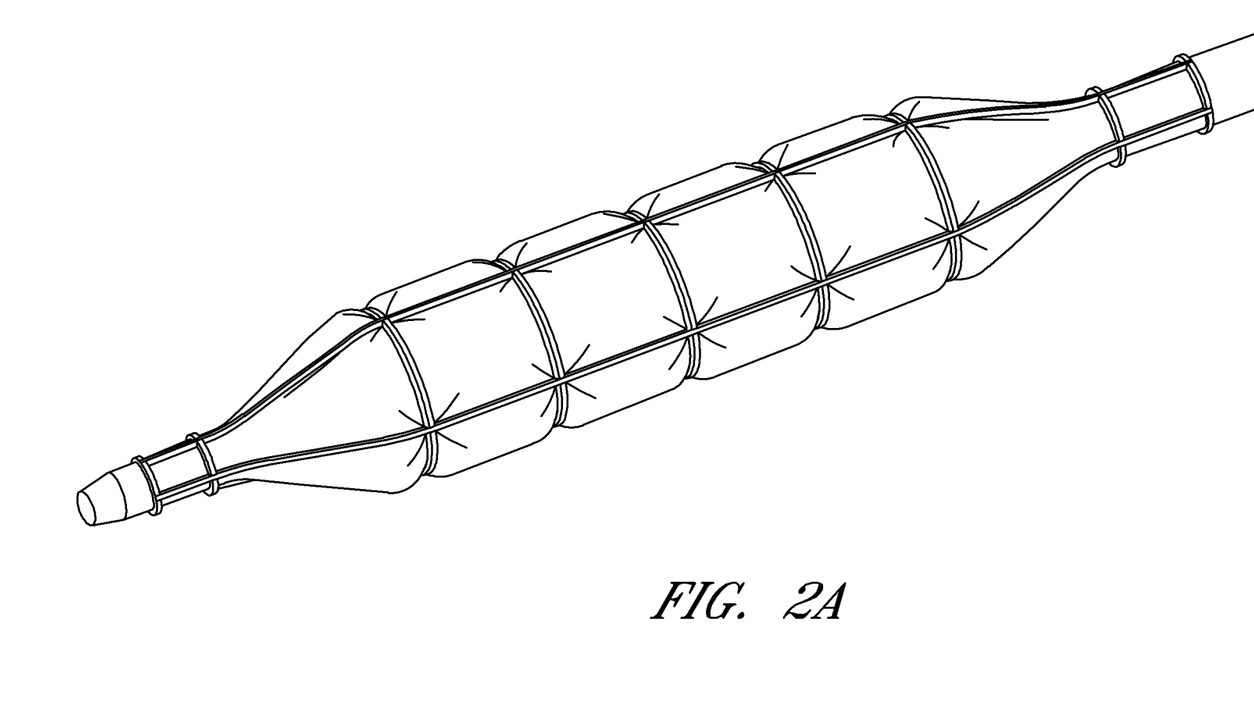
FIGS. 2A and 2B show this invention where a Constraining Structure is located on the balloon creating a controlled topography of hills and valleys during inflation.
Figure 4A:
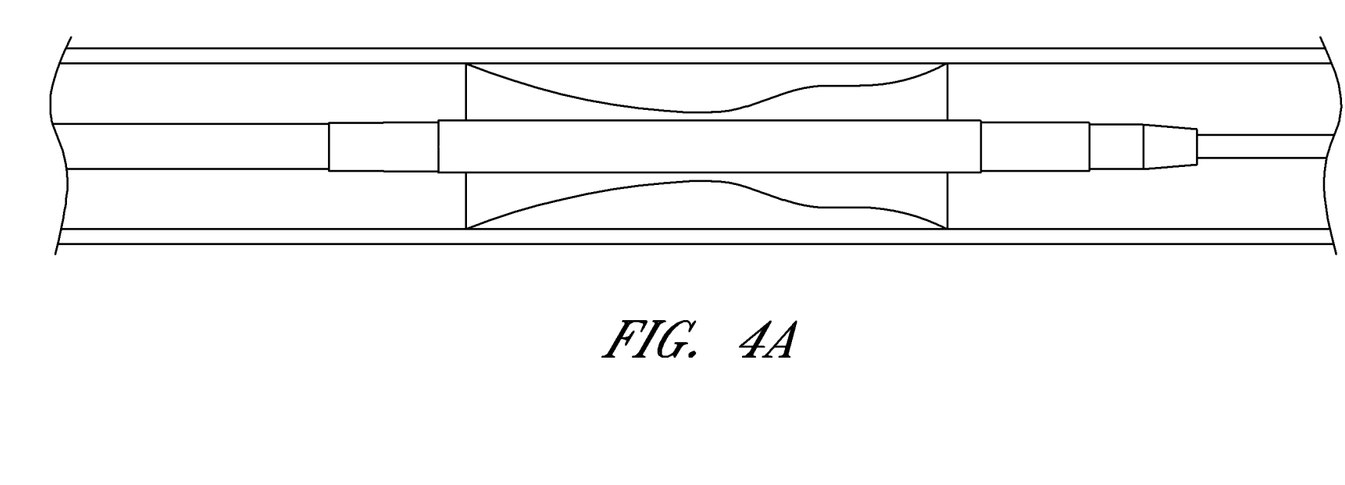
FIGS. 4A to 4C show 3 inflation stages of a conventional balloon.
Figure 4B:
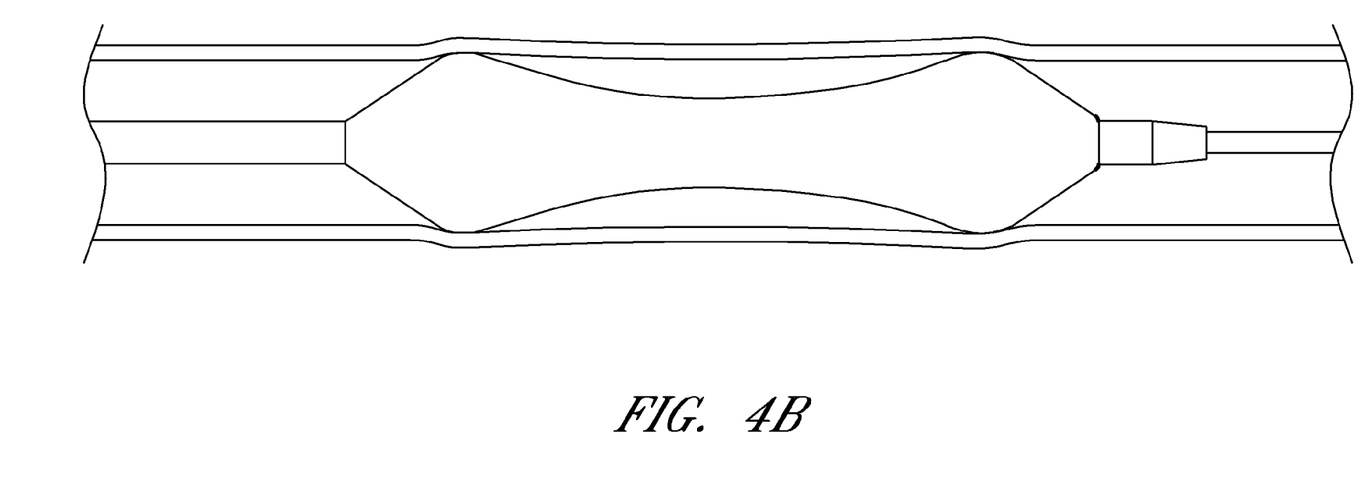
Figure 4C:
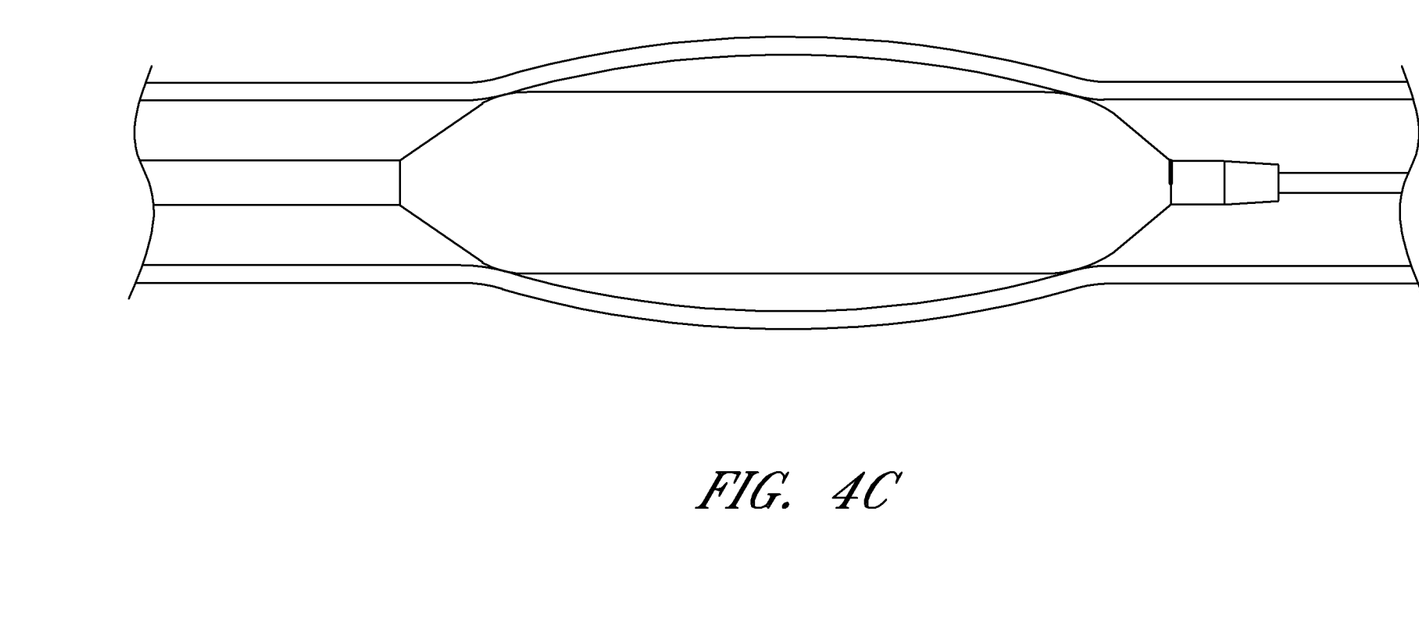

Referring to FIGS. 4A to 4C, in a conventional balloon during inflation, due to balloon compliance, the balloon will expand toward areas of less resistance (healthy areas or areas with less plaque buildup—see FIG. 4B). In order to successfully dilate the lesion additional pressure should be applied until the lesion areas with more severe blockage yields and the balloon can inflate entirely (see FIG. 4C). This process is abrupt and aggressive exposing vessel wall (healthy or diseased areas) to severe trauma and may result in dissection, restenosis and a slower healing process. The topography created by the CS allows for the plaque to gradually re-disperse and flow through the CS valleys (see FIGS. 2A and 2B) while the catheter expands and the inflation is gradual and controlled. The design of the CS allows for plaque remodeling creating less trauma and promotes faster healing.

Figure 2B:
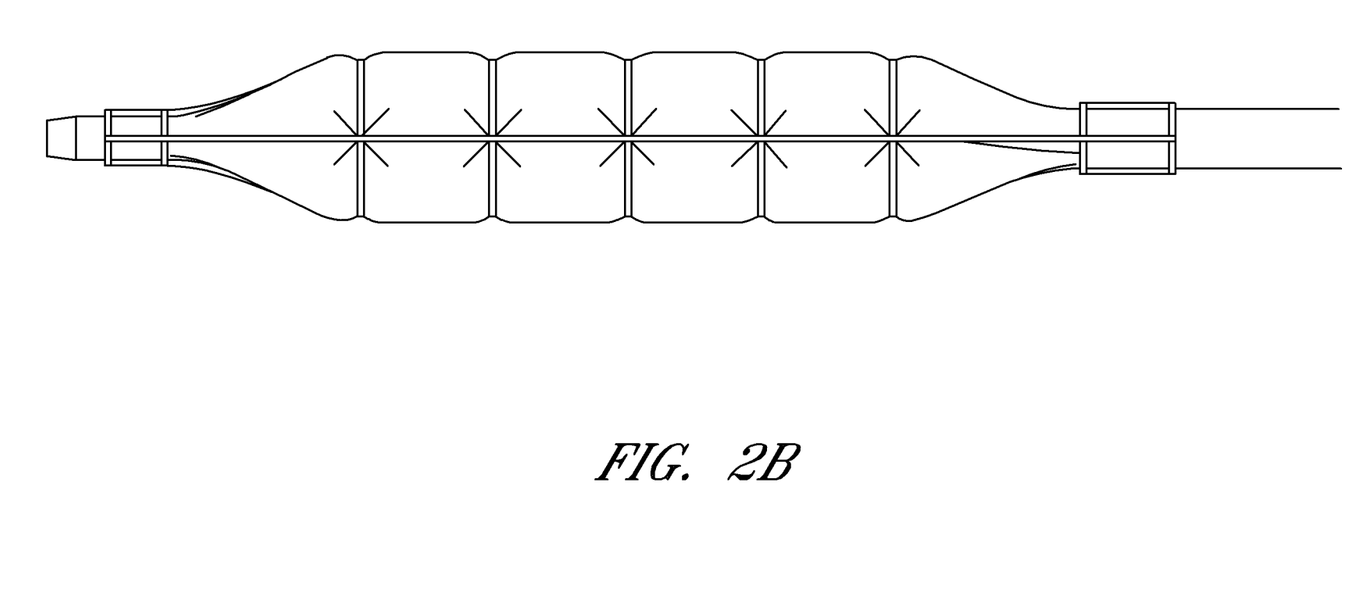
Figure 3A:
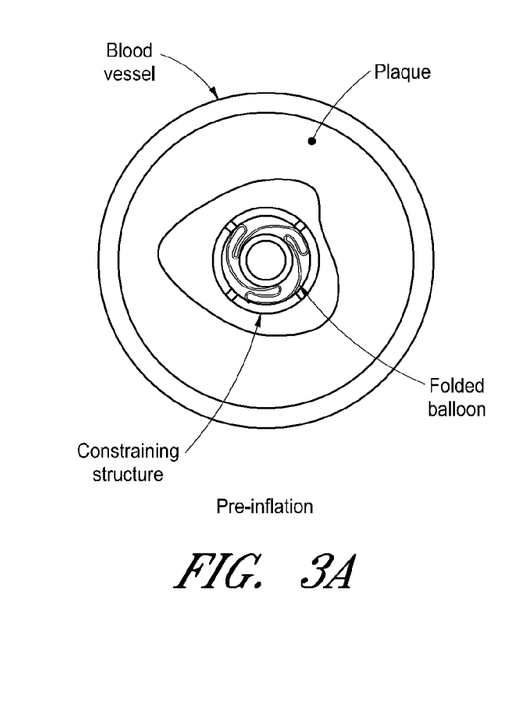
FIGS. 3A to 3C show a cross-section of the dilatation device in this invention during 3 different stages of inflation while unwrapping occur within the constraining device.
Figure 3B:
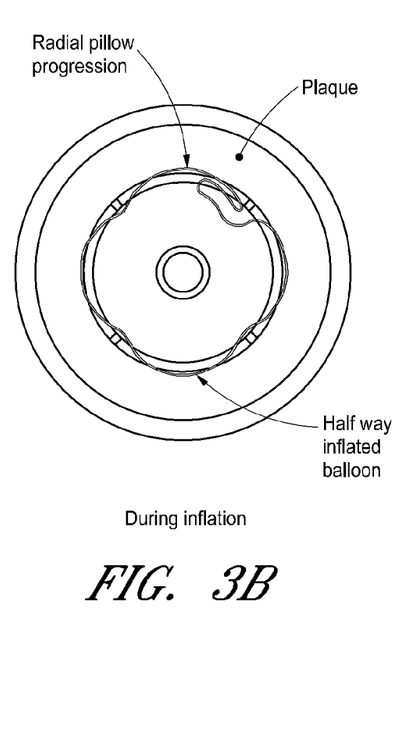
Figure 3C:
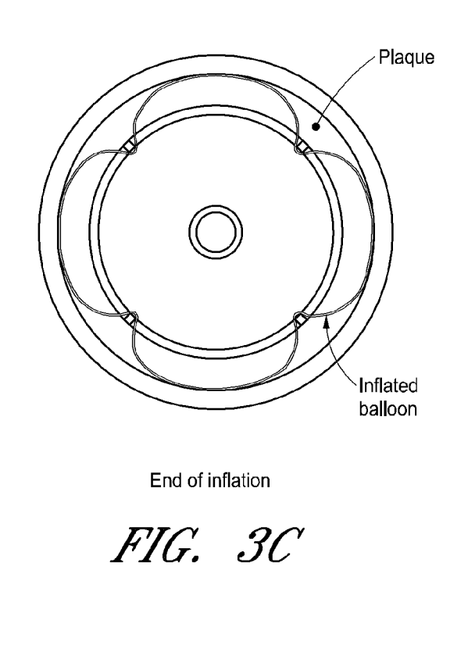

In one embodiment of this invention, the CS is attached to both ends of the balloon and is capable of maintaining a constant length during inflation and deflation processes. During inflation the CS structure expands to a pre-designed diameter that is smaller than the balloon inflated diameter. The balloon continues to expand beyond the CS but is restricted in length by the CS structure. Referring to FIG. 2B, the balloon inflates through the CS structure and is restricted in length by the CS design, thus allowing the device to be inflated without balloon lengthening (common in conventional balloons) thus reducing or eliminating axial forces applied on vessel wall and minimizing trauma to vessel. Furthermore this allows more predictability in inflation process. This is especially effective in long balloons (commonly used in peripheral arteries).

In one embodiment of this invention the CS is constructed of radial rings connecting by axial wires. Upon inflation the CS expands radially without any axial lengthening. This structure allows a compartmental inflation process where the rings create separate inflation zones within the vessel. Therefore the pressure to the vessel wall is controlled and is applied in the radial direction without any strain in the axial direction reducing trauma and possible dissections.

The present invention can be utilized to deliver various agents or active substances particularly (but not limited to) those suitable for treating vascular and other luminal conditions such as antiproliferative and antimitotic agents (such as paclitaxel and sirolimus) other substances can include antibiotics, antiplatelet agents hormones and more.

The active substance can be placed in various designs or techniques such as directly coated on the balloon surface, the CS or both. It can be embedded in a matrix/carrier placed on the balloon or the CS or both. The combination of low trauma dilatation with release of active agent can be superior to drug eluting stents for some portions of the population by minimizing the need for a permanent implant yet providing good long term results.

In one embodiment the balloon surface is coated with drug. Upon balloon inflation, the 'pillows'/hills formed in the balloon external surface coated with drug engage the vessel wall and compress the drug into the wall to facilitate efficient drug delivery to the treated site.

Drug delivery can be facilitated using many different design methods including but not limited to coating the balloon, coating the CS structure or both. Coating with a drug directly or using a carrier in a form of a matrix or microcapsules.

What is claimed is:

1. A system for performing angioplasty comprising:
   a catheter shaft;
   an inflatable balloon at a distal portion of the catheter shaft;
   a radially expandable constraining structure disposed over the balloon, the constraining structure comprising:
      a plurality of axially spaced-apart radially expandable rings comprising a distal radially expandable ring, a proximal radially expandable ring, and at least one additional radially expandable ring between said distal radially expandable ring and said proximal radially expandable ring, each of said plurality of rings being a fully enclosed ring; and
      a plurality of circumferentially spaced-apart axial struts crossing the plurality of rings, each of the axial struts being joined to said catheter on a distal side and/or a proximal side of the balloon, such that the constraining structure is non-deployably disposed over the balloon;
   wherein the constraining structure is capable of maintaining a constant length during inflation and deflation of said balloon when the constraining structure is positioned over said balloon and
   further wherein the constraining structure is configured such that, when the balloon is inflated, a maximum expanded diameter of the constraining structure is less than a maximum inflated diameter of the balloon, such that separate inflation zones are created separated by rings and struts with each of the separate inflation zones being positioned radially outward of the constraining structure.

2. The system of claim 1, wherein the constraining structure comprises a polymer.

3. The system of claim 1, wherein the constraining structure comprises a metal.

4. The system of claim 1, wherein the constraining structure comprises a laser cut structure.

5. The system of claim 1, wherein the constraining structure comprises wires.

6. The system of claim 1, wherein the constraining structure comprises a drug coating.

7. The system of claim 6, wherein the drug coating is directly applied to the constraining structure.

8. The system of claim 6, wherein the drug coating is applied to the constraining structure in a form of a matrix or microcapsule.

9. The system of claim 1, wherein the balloon comprises a drug coating.

10. The system of claim 9, wherein the drug coating is directly applied to the balloon.

11. The system of claim 10, wherein the drug coating is applied to the balloon using a matrix or microcapsule.

12. The system of claim 1, wherein a length of the balloon does not increase during inflation.

13. The system of claim 1, wherein proximal and distal ends of the constraining structure are attached to the catheter shaft.

14. The system of claim 1, wherein prior to the balloon being inflated, the constraining structure has an initial diameter, and wherein when the balloon is deflated, the constraining structure returns to the initial diameter.

* * * * *